US 6,583,087 B2

(12) United States Patent
Ueda

(10) Patent No.: US 6,583,087 B2
(45) Date of Patent: Jun. 24, 2003

(54) AQUEOUS PESTICIDAL COMPOSITION

(75) Inventor: Nobuhito Ueda, Ashiya (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/802,909

(22) Filed: Mar. 12, 2001

(65) Prior Publication Data

US 2001/0031703 A1 Oct. 18, 2001

(30) Foreign Application Priority Data

Mar. 14, 2000 (JP) ........................... 2000-070446

(51) Int. Cl.$^7$ .................... A01N 25/22; A01N 57/02
(52) U.S. Cl. ................... 504/118; 504/127; 504/128; 504/336
(58) Field of Search ................. 504/127, 128, 504/363, 118

(56) References Cited

U.S. PATENT DOCUMENTS

| | | | |
|---|---|---|---|
| 4,853,026 A | 8/1989 | Frisch et al. | ............. 71/86 |
| 4,875,929 A * | 10/1989 | Morgan et al. | ........... 71/121 |
| 4,994,102 A | 2/1991 | Yoshido et al. | ............ 71/86 |
| 5,698,492 A | 12/1997 | Sakaki et al. | .......... 504/128 |
| 5,747,416 A * | 5/1998 | McArdle | ............ 504/115 |
| 6,165,939 A * | 12/2000 | Agbaje et al. | .......... 504/105 |

FOREIGN PATENT DOCUMENTS

| | | |
|---|---|---|
| EP | 0 343 142 A2 | 11/1989 |
| EP | 0 402 770 | 12/1990 |
| EP | 1 095 564 A2 | 5/2001 |
| JP | 07 089817 A | 4/1995 |
| WO | 97-12516 | 4/1997 |
| WO | WO 01/22814 A1 | 4/2001 |

* cited by examiner

*Primary Examiner*—S. Mark Clardy
(74) *Attorney, Agent, or Firm*—Birch Stewart Kolasch & Birch LLP

(57) ABSTRACT

An aqueous herbicidal composition which comprises (a) water-soluble pesticidal ingredient such as herbicidal active ingredient, (b) water-insoluble pesticidal ingredient such as herbicidal active ingredient inhibiting protoporphyrinogenoxidase, (c) at least one selected from nonionic surfactants and anionic surfactants, (d) anionic water-soluble polymer, (e) hydrophobic organic solvent and (f) water is a highly stable aqueous composition in which degradation of the active ingredient is suppressed.

5 Claims, No Drawings

AQUEOUS PESTICIDAL COMPOSITION

FIELD OF THE INVENTION

The present invention relates to an aqueous pesticidal composition.

BACKGROUND ARTS

Currently, various pesticides are utilized in agriculture. For saving labor, two or more pesticides are often applied simultaneously. Pesticidal formulations containing two or more pesticidal ingredient are usually utilized for the above-mentioned application. However, it is generally difficult to prepare a pesticidal formulation comprising a water-soluble pesticidal ingredient and a water-insoluble pesticidal ingredient.

For examples, various herbicides are being utilized for agricultural fields or non-agricultural fields, but since there are various weeds which are target of control and a sole herbicidal active compound is not enough for controlling the various weeds, a combination of plural active compounds is often utilized. Especially, herbicides soluble easily in water represented by glyfosate salts and glufosinate salts are excellent as total herbicide. However, they generally need time to exhibit their herbicidal effect. Therefore, herbicidal compositions combined them with herbicides inhibiting protoporphyrinogenoxidase for adding rapid efficacy are recently suggested in U.S. Pat. No. 5,698,492.

On the other hand, liquid formulations, especially aqueous formulations, are desired by users rather than solid formulations in view of convenience of weighing the formulation when applying. Therefore, the aqueous formulations are widely utilized in a system (bulk delivery system), connected a tank for pesticide formulation with another water tank for dilution by a fastened pipe, to prepare pesticidal application liquid in large fields and so on. Further, the above-mentioned herbicides soluble easily in water are often used as aqueous formulations because of their high water-solubility.

However, many of the above-mentioned herbicides inhibiting protoporphyrinogenoxidase generally tend to decompose in aqueous formulations, and aqueous formulations comprising the herbicide soluble easily in water and the herbicide inhibiting protoporphyrinogenoxidase have insufficient stability (emulsifiable stability, suspensible stability, etc.). As a result, aqueous formulations which hardly decompose and have high stability are desired.

SUMMARY OF THE INVENTION

The present invention provides a stable pesticidal formulation comprising a water-soluble pesticidal ingredient and a water-insoluble pesticidal ingredient, especially a water-soluble herbicidal ingredient and a herbicidal ingredient inhibiting protoporphyrinogenoxidase.

More specifically, the present invention relates to an aqueous pesticidal composition which comprises a water-soluble pesticidal ingredient, water-insoluble pesticidal ingredient, nonionic or anionic surfactant, anionic water-soluble polymer and hydrophobic organic solvent. In the present composition, the decomposition of the pesticidal active ingredients is suppressed for a long time and as a result, the present composition affords high stability.

DISCLOSURE OF THE INVENTION

Namely, the present invention relates to an aqueous composition which comprises (a) water-soluble pesticidal ingredient such as herbicidal active ingredient, (b) water-insoluble pesticidal ingredient such as herbicidal ingredient inhibiting protoporphyrinogenoxidase, (c) at least one selected from nonionic surfactants and anionic surfactants, (d) anionic water-soluble polymer, (e) hydrophobic organic solvent and (f) water.

In the present invention, examples of the pesticidal ingredients include herbicidal compounds, insecticidal compounds, acaricidal compounds, nematocidal compounds, fungicidal compounds, plant growth regulating compounds and insect growth regulating compounds. The term "water-soluble" means 100 g/L or more solubility in water at 20° C. and the term "water-insoluble" means 10 g/L or less solubility in water at 20° C.

Typical water-soluble pesticidal ingredient is an amino acid-type herbicidal active ingredient such as agriculturally acceptable salts of N-(phosphonomethyl)glycine (common name: glyphosate), DL-homoalanin-4-yl(methyl)phosphinic acid (common name: glufosinate) and 4-[hydroxy(methyl) phosphinoyl]-L-homoalanyl-L-alanyl-L-alanine (common name: bialafos). The other examples of the water-soluble herbicidal ingredients include agriculturally acceptable salts of 3-isopropyl-1H-2,1,3-benzothiadiazin-4(3H)-one 2,2-dioxide (common name: bentazone), 3,6-dichloropicolinic acid (common name: clopyrarid), (2,4-dichlorophenoxy) acetic acid (common name: 2,4-D), 3,6-dichloro-2-methoxybenzoic acid (common name: dicamba), 2-(2,4-dichlorophenoxy) propionic acid (common name: dichlorprop), (4-chloro-2-methylphenoxy) acetic acid (common name: MCPA), 4-(4-chloro-O-tolyloxy)butyric acid (common name: MCPB), 2-(4-chloro-2-methylphenoxy)propionic acid (common name: mecoprop) and 4-amino-3,5,6-trichloropicolinic acid (common name: picloram). Examples of the salts include sodium salt, ammonium salt, isopropylammonium salt, trimesium salt and potassium salt.

The water-soluble pesticidal ingredient can be utilized solely or combined two or more, and usually contained in an amount of 15 to 80% by weight, preferably 25 to 65% by weight, more preferably 30 to 60% by weight in the present composition.

Typical water-insoluble pesticidal ingredient is herbicidal ingredient inhibiting protoporphyrinogenoxidase (hereinafter, referred to as PPO active ingredient) that is herbicidal active ingredient which exhibits herbicidal action by inhibiting protoporphyrinogenoxidase enzyme. Examples of the PPO active ingredient include imide type compounds having an N-phenyltetrahydrophthalimide structure, pyridazinone type compounds having a 2-phenylpyridazin-3-one structure, uracil type compounds having a 1-phenylpyrimidin-2,6-dione structure, diphenyl ether type compounds and so on. More concretely, examples of the imide type compound include pentyl [2-chloro-5-(cyclohex-1-en-1,2-dicarboximido)-4-fluorophenoxy] acetate (common name: flumiclorac-pentyl), N-[(7-fluoro-3,4-dihydro-3-oxo-4-(2-propynyl)-2H-1,4-benzoxazin-6-yl)]cyclohex-1-en-1,2-dicarboximide (common name: flumioxazin) and ethyl 2-chloro-3-[2-chloro-5-(1,3-dioxo-4,5,6,7-tetrahydroisoindolin-2-yl) phenyl]acrylate (common name: cinidon-ethyl). Examples of the pyridazinone type compound include ethyl 2-chloro-4-fluoro-5-(5-methyl-6-oxo-4-trifluoromethyl-1,6-dihydropyridazin-1-yl) phenoxyacetate, methyl [2-chloro-4-fluoro-5-[(tetrahydro-3-oxo-1H, 3H-[1,3,4] thiadiazolo[3,4-a]pyridazin-1-ylidene)amino]phenylthio] acetate (common name: fluthiacet-methyl). Examples of the uracil type compound include 1-allyloxycarbonyl-1-methylethyl 2-chloro-5-(3- methyl-2,6-dioxo-4-trifluoromethyl-3,6-dihydro-2H-pyrimidin-1-yl)benzoate (common name: butafenacyl). Examples of the diphenyl ether type compound include ethyl O-[5-(2-chloro-α,α,α-trifluoro-p-tolyloxy)-2-nitrobenzoyl]-DL-lactate (lactofen) and methyl 5-(2,4-dichlorophenoxy)-2-nitrobenzoate (common name: bifenox) ethyl α,2-dichloro-5-[4-(difluoromethyl)-4,5-dihydro-3-methyl-5-oxo-1H-1,2,4-triazol-1-yl]-4-fluorobenzenepropanoate (carfentrazone-ethyl). Examples of the other PPO active ingredient include N-[2,4-dichloro-5-[4-(difluoromethyl)-4,5-dihydro-3-methyl-5-oxo-1H-1,2,4-triazol-1-yl]phenyl]methanesulfonamide (common name: sulfentrazone, ethyl 2-chloro-5-(4-chloro-5-difluoromethoxy-1-methylpyrazol-3-yl)-4-fluorophenoxyacetate (common name: pyraflufen-ethyl) and 2-[2,4-dichloro-5-(2-propynyloxy)phenyl]-5,6,7,8-tetrahydro-1,2,4-triazolo[4,5-a]pyridin-3(2H)-one (common name: azafenidin).

The water-insoluble pesticidal ingredient can be utilized solely or combined two or more, and usually contained in an amount of 0.1 to 30% by weight, preferably 0.3 to 20% by weight in the present composition.

In the present composition, the surfactant is at least one selected from nonionic surfactants and anionic surfactants. Typical examples of the nonionic surfactant include sugar ester type nonionic surfactants, fatty acid ester type nonionic surfactants, vegetable oil type nonionic surfactants, alcohol type nonionic surfactants, alkylphenol type nonionic surfactants, polyoxyethylene-polyoxypropylene block polymer type nonionic surfactants, bisphenol type nonionic surfactants, polyaromatic ring type nonionic surfactants, silicone type nonionic surfactants and fluorine type nonionic surfactants.

The sugar ester type nonionic surfactants are exemplified by sorbitan fatty acid esters, polyoxyethylenesorbitan fatty acid esters and sucrose fatty acid esters. The fatty acid ester type nonionic surfactants are exemplified by polyoxyethylene fatty acid esters, polyoxyethylene resin acid esters and polyoxyethylene fatty acid diesters. The vegetable oil type nonionic surfactants are exemplified by polyoxyethylene castor oil and hydrogenated polyoxyethylene castor oil. The alcohol type nonionic surfactants are exemplified by polyoxyethylenealkyl ethers. The alkylphenol type nonionic surfactants are exemplified by polyoxyethylenealkyl phenyl ethers, polyoxyethylenedialkyl phenyl ethers and polyoxyethylenealkyl phenyl ether-formalin condensates. The polyoxyethylene-polyoxypropylene block polymer type nonionic surfactants are exemplified by polyoxyethylene-polyoxypropylene block polymers, alkylpolyoxyethylene-polyoxypropylene block polymer ethers and alkylphenylpolyoxyethylene-polyoxypropylene block polymer ethers. The bisphenol type nonionic surfactants are exemplified by polyoxybisphenyl ethers. The polyaromatic ring type nonionic surfactants are exemplified by polyoxyalkylenebenzyl phenyl ethers and polyoxyalkylenestyryl phenyl ethers. The silicone type nonionic surfactants are exemplified by polyoxyethylene ether type silicone surfactants and polyoxyethylene ester type silicone surfactants.

Typical examples of the anionic surfactant include sulfate type anionic surfactants, sulfonate type anionic surfactants and phosphate type anionic surfactants. The sulfate type anionic surfactants are exemplified by alkyl sulfates, polyoxyethylenealkyl ether sulfates, polyoxyethylenealkyl phenyl ether sulfates, polyoxystyryl phenyl ether sulfates and polyoxyethylene-polyoxypropylene block polymer sulfates. The sulfonate type anionic surfactants are exemplified by paraffinsulfonates, dialkyl sulfosuccinates, alkylbenzenesulfonates, monoalkylnaphthalenesulfonates, dialkylnaphthalenesulfonates, naphthalenesulfonate-formalin condensates, alkyl diphenyl ether disulfonates, ligninsulfonates and polyoxyethylenealkyl phenyl ether sulfonates. The phosphate type anionic surfactants are exemplified by polyoxyethylenealkyl ether phosphates, polyoxyethylenemonoalkyl phenyl ether phosphates, polyoxyethylenedialkyl phenyl ether phosphates, polyoxyethylenestyryl phenyl ether phosphates, polyoxyethylene-polyoxypropylene block polymer phosphates and alkylphosphates.

In the present composition, the use of the anionic surfactants is preferable in view of storage stability. The sulfate type anionic surfactants are preferable in the anionic surfactants. Further, preferable are alkoxysulfate type anionic surfactants, alkylsulfate type anionic surfactants and alkoxyalkylsulfate type anionic surfactants. Furthermore, the alkylsulfate type anionic surfactants having 10 to 14 of the carbon number are more preferable. When the nonionic surfactants are used in the present composition, the use of fatty alcohol type nonionic surfactants are preferable in view of herbicidal effect. Especially, fatty alcohol ethers are preferable and fatty alcohol polyglycol ethers are more preferable. These nonionic/anionic surfactants are usually contained in an amount of 0.1 to 30% by weight, preferably 1 to 20% by weight, more preferably 3 to 10% by weight in the present composition.

The anionic water-soluble polymer in the present composition usually has at least one functional group selected from sulfonic acid group, carboxylic acid group, phosphonic acid group, boric acid group and sulfuric acid group in the molecule. These functional groups exist in the anionic water-soluble polymer as a form of dissociated acid, undissociated acid or salt. In the present invention, the anionic water-soluble polymer having carboxylic acid group is preferable.

Further, the anionic water-soluble polymer in the present composition has, for example, sugar structure, alkyl structure or the like in the main chain structure. Among them, the preferable one is sugar structure, namely polysaccharides. Examples of said anionic water-soluble polymer include gum arabic, xanthan gum, locust gum, alginic acid and its salts, carboxymethylcellulose and its salts, and ligninsulfonic acid salts.

Molecular weight of the anionic water-soluble polymer in the present composition is in the range that is acceptable as pesticide formulation, and usually 2000 to 1000000, preferably 10000 to 100000.

Viscosity of the anionic water-soluble polymer in the present composition is usually 10000 mPa·s or less, preferably 5000 mPa·s or less as 1% aqueous solution at 20° C. in view of handling. The anionic water-soluble polymer is usually contained in an amount of 0.1 to 20% by weight, preferably 0.5 to 10% by weight, more preferably 1 to 5% by weight in the present composition.

The hydrophobic organic solvent utilized in the present invention is usually a solvent having 10 g/L or less water-solubility at 20° C. Examples of the hydrophobic organic solvent include aromatic solvents, animal oil and vegetable oil solvents, paraffin solvents and ester solvents.

Examples of the aromatic solvent include xylene, alkylbenzenes and alkylnaphthalenes, and examples of the animal oil and vegetable oil solvent include rapeseed oil, soybean oil and linseed oil. Examples of the paraffin solvent include normal paraffin having 5 or more of carbon number, isoparaffin having 5 or more of carbon number and cycloparaffin having 5 or more of carbon number, preferably normal paraffin having 5 to about 70 of carbon number, isoparaffin having 5 to about 200 of carbon number and cycloparaffin having 5 to about 200 of carbon number, more preferably normal paraffin having 5 to about 45 of carbon number, isoparaffin having 5 to about 100 of carbon number and cycloparaffin having 5 to about 100 of carbon number.

In the present composition, the hydrophobic organic solvent is utilized solely or combined two or more. For the hydrophobic organic solvent for the EW formulation described later, aromatic solvents are preferable in view of high solubility, especially the aromatic solvents having 70° C. or more, preferably 120° C. or more, of flashing point. For the hydrophobic organic solvent for the SE formulation described later, aliphatic solvents are preferable in view of low solubility, especially isoparaffin, cycloparaffin and ester solvents. Further, when the hydrophobic organic solvent is utilized in the present composition, the amount is decided by depending on formulation type, object for use and so on, and is usually 0.1 to 500 times, preferably 1 to 100 times, more preferably 2 to 50 times by weight against water-insoluble pesticidal ingredient. The content of the hydrophobic organic solvent is usually 0.1 to 50% by weight, preferably 1 to 30% by weight in the present composition.

Typical examples of the hydrophobic organic solvent include Hisol SAS-296 (a mixture of 1-phenyl-1-xylylethane and 1-phenyl-1-ethylphenylethane, commercial name of Nippon Petroleum Company), Hisol SAS-LH (commercial name of Nippon Petroleum Company), Shellsol A (commercial name of Shell Chemical Corporation), Shellsol AB (commercial name of Shell Chemical Corporation), Shellsol E (commercial name of Shell Chemical Corporation), Shellsol R (commercial name of Shell Chemical Corporation), Shellsol T (commercial name of Shell Chemical Corporation), Shellsol D-70 (commercial name of Shell Chemical Corporation), Cactus Solvent HP-MN (containing 80% of methylnaphthalene, commercial name of Nikko Petrochemical Company), Cactus Solvent HP-DMN (containing 80% of dimethylnaphthalene, commercial name of Nikko Petrochemical Company), Cactus Solvent P-100 (alkylbenzene having 9 to 10 of carbon number, commercial name of Nikko Petrochemical Company), Cactus Solvent P-150 (alkylbenzene, commercial name of Nikko Petrochemical Company), Cactus Solvent P-180 (a mixture of methylnaphthalene and dimethylnaphthalene, commercial name of Nikko Petrochemical Company), Cactus Solvent P-200 (a mixture of methylnaphthalene and dimethylnaphthalene, commercial name of Nikko Petrochemical Company), Cactus Solvent P-220 (a mixture of methylnaphthalene and dimethylnaphthalene, commercial name of Nikko Petrochemical Company), Cactus Solvent PAD-1 (dimethylmonoisopropylnaphthalene, commercial name of Nikko Petrochemical Company), Solvesso 100 (aromatic hydrocarbon, commercial name of ExxonMobil Chemical), Solvesso 150 (aromatic hydrocarbon, commercial name of ExxonMobil Chemical), Solvesso 200 (aromatic hydrocarbon, commercial name of ExxonMobil Chemical), Suwasol 100 (toluene, commercial name of Maruzen Petroleum Company), Suwasol 200 (xylene, commercial name of Maruzen Petroleum Company), Vinycizer 20 (diisotridecyl phthalate, commercial name of Kao Corporation), Vinycizer 40 (diisobutyl adipate, commercial name of Kao Corporation), Vinycizer 50 (diisodecyl adipate, commercial name of Kao Corporation), Vinycizer 85 (dialkyl phthalate, commercial name of Kao Corporation), Vinycizer 105 (didecyl phthalate, commercial name of Kao Corporation), Vinycizer 124 (dialkyl phthalate, commercial name of Kao Corporation), Excepal O-OL (octyl oleate, commercial name of Kao Corporation), Excepal L-OL (lauryl oleate, commercial name of Kao Corporation), Excepal OD-OL (octyldodecyl oleate, commercial name of Kao Corporation), Toxanon PP-1000 (polyoxypropylene glycol, commercial name of Sanyo Chemical Industries), Nikkol IPA-A (isopropyl myristate, commercial name of Nikko Chemical Company), Nikkol IPA-EX (isopropyl myristate, commercial name of Nikko Chemical Company), Teclean N-30 (commercial name of Nippon Petroleum Company), Teclean N-32 (commercial name of Nippon Petroleum Company), Teclean N-33 (commercial name of Nippon Petroleum Company), Mineral oil 46P (commercial name of Nichibeikoyu Company), Pesticidal mineral oil P (commercial name of Nichibeikoyu Company), Pesticidal oil H (commercial name of Nichibeikoyu Company), Super oil A (commercial name of Nichibeikoyu Company), Super oil B (commercial name of Nichibeikoyu Company), Super oil C (commercial name of Nichibeikoyu Company), Super oil D (commercial name of Nichibeikoyu Company), Super oil E (commercial name of Nichibeikoyu Company), Super oil F (commercial name of Nichibeikoyu Company), Spindle oil No.1 (commercial name of Nichibeikoyu Company), Spindle oil No.2 (commercial name of Nichibeikoyu Company), Mineral oil B (commercial name of Nichibeikoyu Company), Mineral oil C (commercial name of Nichibeikoyu Company), Naphthesol M (naphthene/isoparaffin/normalparaffin/aroma=75% or more/5–10%/10% or less/5% or less, commercial name of Nippon Petrochemical Company), Isosol 300 (commercial name of Nippon Petrochemical Company), Isosol 400 (commercial name of Nippon Petrochemical Company), Exxol D80 (a mixture of paraffin and cycloparaffin, commercial name of ExxonMobil Chemical), Exxol D110 (a mixture of paraffin and cycloparaffin, commercial name of ExxonMobil Chemical), Exxol D130 (a mixture of paraffin and cycloparaffin, commercial name of ExxonMobil Chemical), Exxol D160 (a mixture of paraffin and cycloparaffin, commercial name of ExxonMobil Chemical), Isopar E (kerosene, commercial name of ExxonMobil Chemical), Isopar G (kerosene, commercial name of ExxonMobil Chemical), Isopar H (kerosene, commercial name of ExxonMobil Chemical), Isopar M (kerosene, commercial name of ExxonMobil Chemical), Neo-Chiozol (kerosene, commercial name of Chuo Chemical Company), IP Solvent 2028 (isoparaffin oil, Idemitsu Petrochemical Company), IP Solvent 2835 (isoparaffin oil, Idemitsu Petrochemical Company), Naplex 38 (naphthene oil, commercial name of Mobil Petroleum Corporation), Whitelex 205 (commercial name of Mobil Petroleum Corporation), Whitelex 207 (commercial name of Mobil Petroleum Corporation), Whitelex 215 (commercial name ExxonMobil Chemical), Whitelex 247 (commercial name of ExxonMobil Chemical), Whitelex 2210 (commercial name of ExxonMobil Chemical), Whitelex 307 (commercial name of ExxonMobil Chemical), Whitelex 309 (commercial name of ExxonMobil Chemical) and Whitelex 326 (commercial name of ExxonMobil Chemical), and Whitelex 335 (commercial name of ExxonMobil Chemical).

The present composition comprises (a) water-soluble pesticidal ingredient, (b) water-insoluble pesticidal ingredient, (c) at least one selected from nonionic surfactants and anionic surfactants solvent, (d) anionic water-soluble polymer, (e) hydrophobic organic, (f) water and optionally viscosity adjusting agent, antifoaming agent, antifreezing agent, preservative, stabilizing agent, coloring agent, perfume, synergist, safener and so on.

The content of water is usually 20 to 90% by weight, preferably 25 to 85% by weight in the present composition.

The viscosity adjusting agents utilized in the present composition are exemplified by natural polysaccharides such as xanthan gum, lamxan gum, locust bean gum, carrageenan and werant gum; synthetic polymers such as sodium polyacrylate; semi-synthetic polymers such as carboxymethylcellulose; mineral powders such as aluminum silicate, smectite, bentonite, hectorite and anhydrous silica; and alumina sol. Examples of the xanthan gum include Kelzan S (manufactured by Monsanto) and examples of the aluminum silicate include Veegum R (manufactured by Vanderbilt). Further, examples of the anhydrous silica include Aerosil 200 (manufactured by Degussa Huls) and examples of the mixture of anhydrous silica and alumina sol include Aerosil COK-84 (manufactured by Degussa Huls). When the viscosity adjusting agent is utilized, the amount is usually 0.01 to 10% by weight, preferably 0.1 to 5% by weight in the present composition. Further, these viscosity adjusting agents are preferably added to the present composition before adding the herbicidal active ingredient soluble easily in water in order to be enough dissolved and/or wetted with water for obtaining thickening effect in a small amount.

Examples of the antifoaming agent utilized in the present composition include silicone type antifoaming agents such as Antifoam C (commercial name of Dow Corning Corporation), Antifoam CE (commercial name of Dow Corning Corporation), TSA730 (commercial name of Toshiba Silicone Company), TSA731 (commercial name of Toshiba Silicone Company), TSA732 (commercial name of Toshiba Silicone Company), and YMA6509 (commercial name of Toshiba Silicone Company); and fluorine type antifoaming agents such as Fluowet PL80 (commercial name of Clariant Company). When the antifoaming agent is utilized, the amount is usually 0.001 to 3% by weight in the present composition.

Examples of the antifreezing agent utilized in the present include water-soluble glycols such as propylene glycol. When the antifreezing agent is utilized, the amount is usually 0.5 to 30% by weight, preferably 1 to 20% by weight, more preferably 5 to 10% by weight in the present composition.

Examples of the preservative utilized in the present include p-hydroxybenzoate esters, salicylic acid derivatives and isothiazolin-3-one derivatives. When the preservative is utilized, the amount is usually 0.01 to 5% by weight, preferably 0.05 to 3% by weight, more preferably 0.1 to 1% by weight in the present composition.

The present composition is an aqueous pesticidal composition which comprises (a) water-soluble pesticidal ingredient, (b) water-insoluble pesticidal ingredient, (c) nonionic surfactant or anionic surfactant, (d) anionic water-soluble polymer and (e) hydrophobic organic solvent, and wherein the above-mentioned (a) water-soluble pesticidal ingredient, (b) water-insoluble active pesticidal ingredient, (c) nonionic surfactant or anionic surfactant, (d) anionic water-soluble polymer and (e) hydrophobic organic solvent exist in a solvent mainly consisting of water.

In the present composition, the water solvent forms a continuous phase (aqueous phase) and the water-soluble pesticidal ingredient usually exists in the aqueous phase in a state dissolved in water. The water-insoluble pesticidal ingredient is not essentially dissolved in the aqueous phase and it is dispersed in the aqueous phase. The present composition can be various formulations corresponding to a dispersing state of the water-insoluble pesticidal ingredient.

With regard to the formulation type of the present composition, there are a case wherein the water-insoluble pesticidal ingredients are suspended in the aqueous phase as solid particles, and another case wherein the water-insoluble pesticidal ingredients are emulsified in the aqueous phase as liquid particles.

The formulation type, wherein the water-insoluble pesticidal ingredients are suspended in the aqueous phase as solid particles, include a capsule suspension formulation wherein oil drops dissolving the water-insoluble pesticidal ingredients in a solvent are encapsulated and suspended in the aqueous phase, a suspoemulsion formulation wherein the solid water-insoluble pesticidal ingredients are suspended in the aqueous phase and solvent is emulsified in the aqueous phase, and a capsule suspoemulsion formulation wherein the encapsulated solid or liquid water-insoluble pesticidal ingredients are suspended in the aqueous phase and solvent is emulsified in the aqueous phase.

On the other hand, the formulation type, wherein the water-insoluble pesticidal ingredients are suspended in the aqueous phase as liquid particles, include an emulsion formulation wherein liquid water-insoluble pesticidal ingredients are emulsified in the aqueous phase, an emulsion formulation wherein oil drops dissolving solid water-insoluble pesticidal ingredients in a hydrophobic organic solvent are emulsified in the aqueous phase, and a suspoemulsion formulation wherein oil drops suspending the solid water-insoluble pesticidal ingredients in a hydrophobic organic solvent are emulsified in the aqueous phase.

Capsule suspension formulation (hereinafter, may be referred as to CS formulation) is a formulation wherein fine particles (microcapsules) having a volume median diameter of about one $\mu$m to about one hundred $\mu$m, which are encapsulated active ingredient in a wall substance, are suspended in water. Examples of the wall substance which forms microcapsules include polyurea, polyurethane, polyamide, urea-formalin resin, melamine-formalin resin, gelatin, albumin and chitosan. When the present composition is a CS formulation, the microcapsules containing the water-insoluble pesticidal ingredients which are usually prepared to have a volume median diameter of 0.1 to 50 $\mu$m, preferably 0.5 to 40 $\mu$m, more preferably 1 to 30 $\mu$m are dispersed in an aqueous phase which comprises a water-soluble active ingredient, surfactant and anionic water-soluble polymer.

Examples of the microencapsulation method include known methods such as interfacial polymerization method, In-situ method, phase separation (coacervation) method and solvent evaporation method.

Interfacial polymerization method is a method for preparing microcapsules by dissolving each monomer in two solvents which cannot be mixed each other, and allowing the monomers to react at the interface of the solvents for affording polymer by interfacial polymerization reaction. In-situ method is generally a method for preparing microcapsules by dissolving monomer, and optionally catalyst, in one of two solvents which cannot be mixed each other, and polymerizing at the interface of the solvents for forming uniform wall on the surface of the core substance.

Phase separation (coacervation) method is generally a method for preparing microcapsules by utilizing a phenomenon (coacervation) separating a thicker phase with a thinner phase by a slight change of solvent components of polymer solution and allowing one or more polymer colloid to precipitate at the interface and form wall by addition of a phase-separation inducing agent that has a high affinity with solvent, by joint electrostatic action or by hydrogen bonding.

Solvent evaporation method is generally a method for preparing microcapsules by dispersing core liquid or core solid, that can form a wall material, in a solvent dissolving polymer, further dispersing it in another solvent that cannot be mixed with the above solvent, and then evaporating gradually the above solvent to deposit polymer at the interface of the core substance.

These microencapsulation methods and kind of wall materials are selected suitably for the object. When a water-insoluble pesticidal ingredient is microencapsulated, the water-insoluble pesticidal ingredient can be dissolved or suspended in a water-insoluble solvent at advance, if necessary. When the present composition is a CS formulation, it is generally obtained by mixing a surfactant, anionic water-soluble polymer, water-soluble active ingredient and water, and optionally viscosity adjusting agent, antifoaming agent, antifreezing agent, preservative and so on, adding aqueous dispersion of microcapsules prepared at advance to the mixture and dispersing the microcapsules by using stirrer such as chemical mixer.

When the water-insoluble solvent is emulsified in the present composition and the water-insoluble pesticidal ingredient is dispersed inside or outside of the hydrophobic organic solvent phase, droplets of the hydrophobic organic solvent phase (hereinafter, referred as to suspoemulsion particles) are combined with aqueous phase to form emulsion and the water-insoluble pesticidal ingredient is dispersed in the suspoemulsion particles or in the aqueous phase in the present composition. Such a typical formulation is suspoemulsion formulation (hereinafter referred as to SE formulation). The suspoemulsion particles are emulsified in the present composition to form emulsion with aqueous phase containing water-soluble active ingredient, nonionic or anionic surfactant and anionic water-soluble polymer. The water-insoluble pesticidal ingredient in the SE formulation usually has a volume median diameter of 0.1 to 50 $\mu$m, preferably 0.3 to 30 $\mu$m, more preferably 0.5 to 20 $\mu$m.

When the present composition is an SE formulation, it can be obtained by dissolving an anionic water-soluble polymer in water, adding a surfactant, water-insoluble pesticidal ingredient, water-soluble active ingredient, hydrophobic organic solvent which cannot essentially dissolve the water-insoluble pesticidal ingredient, and optionally auxiliaries such as viscosity adjusting agent, antifoaming agent, antifreezing agent, preservative and so on thereto, mixing them, and then pulverized, dispersed and emulsified simultaneously by a procedure of wet grinding using a media such as glass beads and zirconia. Further, an emulsion and suspension are prepared by separation and then mixing them also can give the SE formulation. Furthermore, it is exemplified by a method of preparing an emulsion and pulverizing and dispersing the water-insoluble pesticidal ingredient in the emulsion, and a method of preparing a suspension in which the water-insoluble pesticidal ingredient is pulverized and dispersed and emulsifying a hydrophobic organic solvent in the suspension.

When a water-insoluble pesticidal ingredient is dissolved in hydrophobic organic solvent and the solvent phase is dispersed in an aqueous phase, the present composition is a composition wherein the water-insoluble pesticidal ingredient is dissolved in droplets of the hydrophobic organic solvent and the droplets dissolving the water-insoluble pesticidal ingredient are emulsified in the aqueous phase. Further, when the water-insoluble pesticidal ingredient is dispersed in the aqueous phase as a state of liquid, the present composition is a composition wherein droplets of the water-insoluble pesticidal ingredient are emulsified in the aqueous phase (hereinafter, both of the droplets the water-insoluble pesticidal ingredient and the droplets dissolving the water-insoluble pesticidal ingredient may be referred as to emulsion particles). A typical formulation of these compositions is an emulsion formulation (hereinafter, referred as to EW formulation).

When a water-insoluble pesticidal ingredient is solid or semi-solid at ordinary temperature, the water-insoluble pesticidal ingredient is dissolved in water-insoluble solvent at advance and the solution is emulsified and dispersed in water to give EW formulation. When water-insoluble pesticidal ingredient is liquid at ordinary temperature, the water-insoluble pesticidal ingredient or the solution dissolving the water-insoluble pesticidal ingredient is emulsified and dispersed in water to give EW formulation. The emulsion particles are usually adjusted to have a volume median diameter of 0.1 to 50 $\mu$m, preferably 0.3 to 40 $\mu$m, more preferably 0.5 to 30 $\mu$m, and dispersed in the aqueous phase containing a water-soluble active ingredient, surfactant and water-soluble polymer.

The present composition that is an emulsion formulation can be obtained as follows. When a water-insoluble pesticidal ingredient is dissolved in water-insoluble solvent, the emulsion formulation can be obtained by dispersing the solution dissolving the water-insoluble pesticidal ingredient in a mixture of a surfactant, anionic water-soluble polymer, water-soluble active ingredient, water and optionally viscosity adjusting agent, antifoaming agent, antifreezing agent, preservative and so on by using a stirrer such as homogenizer. On the other hand, when a water-insoluble pesticidal ingredient is liquid at ordinary temperature and water-insoluble solvent is not utilized, the emulsion formulation can be obtained by directly dispersing the water-insoluble pesticidal ingredient in a mixture of a surfactant, ionic water-soluble polymer, water-soluble active ingredient, water and optionally viscosity adjusting agent, antifoaming agent, antifreezing agent, preservative and so on by using a stirrer such as homogenizer.

In the present composition containing a water-insoluble solvent, the desired type formulation (SE formulation, EW formulation) can be prepared by suitably selecting a kind or amount of the water-insoluble solvent. For example, a water-insoluble solvent of a kind and amount that can be dissolve the used water-insoluble pesticidal ingredient makes the present composition EW formulation, and a water-insoluble solvent that cannot be essentially dissolve the solid or semi-solid water-insoluble pesticidal ingredient gives SE formulation. The use of the water-insoluble solvent in an amount less than a solubility of the water-insoluble pesticidal ingredient also gives SE formulation.

When the water-soluble pesticidal ingredient is a water-soluble herbicidal ingredient and the water-insoluble pesticidal ingredient is a PPO active ingredient, examples of the weeds controlled by the present composition include broadleaf weeds such as wild buckwheat (*Polygonum convolvulus*), pale smartweed (*Polygonum lapathifolium*), docks (*Rumex crispus*), common purslane (*Portulaca oleracea*), common chickweed (*Stellaria media*), *Malachium aquaticum,* common lambsquarters (*Chenopodium album*), redroot pigweed (*Amaranthus retroflexus*), wild mustard (*Sinapis arvensis*), shepherdpurse (*Capsella bursa-pastoris*), hemp sesbania (*Sesbania exaltata*), sicklepod (*Cassia obtusifolia*), *Torilis japonica,* velvetleaf (*Abutilon theophrasti*), prickly sida (*Sida spinosa*), field pansy (*Viola arvensis*), catchweed bedstraw (cleavers) (*Galium aparine*), ivyleaf morningglory (*Ipomoea hederacea*), tall morningglory (*Ipomoea purpurea*), field bindweed (*Convolvulus* arvensis), purple deadnettle (*Lamium purpureum*), henbit (*Lamium amplexicaule*), jimsonweed (*Datura stramonium*), black nightshade (*Solanum nigrum*), persian speedwell (*Veronica persica*), common cocklebur (*Xanthium pensylvanicum*), common sunflower (*Helianthus annuus*), scentless chamomile (*Matricaria perforata* or *inodora*), corn marigold (*Chrysanthemum segetum*), Japanese mugwort (*Artemisia princeps*), tall goldenrod (*Solidago altissima*), corn spurry (*Spergula arvensis*) and so on; Graminaceous weeds such as *Agropyron tsukushiense,* barnyardgrass (*Echinochloa crus-galli*), green foxtail (*Setaria viridis*), giant foxtail (*Setaria faheri*), large crabgrass (*Digitaria sanguinalis*), annual bluegrass (*Poa annua*), blackgrass (*Alopecurus myosuroides*), oats (*Avena sativa*), wild oats (*Avena fatua*), johnsongrass (*Sorghum halepense*), quackgrass (*Agropyron repens*), downy brome (*Bromus tectorum*), bermudagrass (*Cynodon dactylon*); Spiderworts (Commelinaceous weeds) such as common dayflower (*Commelina communis*); and Sedges (Cyperaceous weeds) such as rice flatsedge (*Cyperus iria*) and purple nutsedge (*Cyperus rotundus*). The present composition can be utilized as herbicide in farm, open field, ridge of paddy field, orchard, pasture, lawn, forest or non-cultivating field. For example, the present composition can be applied to soil treatment, foliar treatment or flooding treatment before or after the emergence of weeds. The soil treatment may include a soil surface treatment and a soil incorporation treatment and the foliar treatment may include an application over the plants and a directed application in which it is applied only to weeds so as to keep off the crop plants. The present composition can be utilized for any treatment. In a paddy field, the present composition can be applied to paddy water or its inlet directly without diluting in application. Further, the dilution of the present composition for application can be used for aerial application by helicopter, plane or radio-controlled helicopter. The dosage of the present composition, although it may vary with the mixing ratio of active ingredients, formulation types, kinds of objective weeds, weather conditions and so on, is usually in the range of 100 to 20000 g, preferably 500 to 8000 g, as the total amount of the active ingredient compounds per hectare. The present composition may be applied with auxiliaries such as spreading agent. Examples of the spreading agent include liquid nitrogen, Agridex (commercial name of Helena Chemical Corporation), Dynamic (commercial name of Helena Chemical Corporation), Induce (commercial name of Helena Chemical Corporation) and Silwet L-77 (manufactured by Nihon Unicar).

EXAMPLES

Hereinafter, the present invention is explained in more detail referring to an example but the present invention should not be limited in the following examples.

Example 1

In 300 g of aromatic hydrocarbon (manufactured by ExxonMobil Chemical, commercial name: Solvesso 200), 6.8 g of flumicrolac-pentyl was dissolved to afford a homogeneous solution, to which 100 g of sodium alkylsulfate/EO 2 mol (manufactured by Rodia Corporation, commercial name: Rodapex N70K) was added and stirred at 500 rpm by T. K. Autohomomixer (commercial name, disperser manufactured by Tokushukikakogyo) at room temperature for 10 minutes. Under stirring by T. K. Autohomomixer (room temperature, 500 rpm), 249 g of aqueous gum arabic solution of 8% by weight was gradually added to the dispersion and continued to stir (5000 rpm) at room temperature for 10 minutes to afford a homogeneous emulsion slurry. Then, under stirring by T. K. Autohomomixer (room temperature, 5000 rpm), 774.2 g of aqueous glypnosate isopropylammonium salt solution (purity 62%) and 20 g of silica/aluminum oxide mixture (manufactured by Degussa Huls, commercial name: Aerosil COK-84) were added to the slurry, and further stirred (5000 rpm) at room temperature for 10 minutes to afford a present composition.

Example 2

The same procedure was performed as Example 1, except that sodium alkylsulfate/EO 3 mol (manufactured by Rodia Corporation, commercial name: Rodapex 3N70) was used in place of sodium alkylsulfate/EO 2 mol, to afford a present composition.

Example 3

The same procedure was performed as Example 1, except that aliphatic alcohol polyglycol ether (manufactured by Clariant Company, commercial name: Emulsogen M) was used in place of sodium alkylsulfate/EO 2 mol and that 179 g of aqueous gum arabic solution of 11.2% by weight was used in place of 249 g of aqueous gum arabic solution of 8% by weight, to afford a present composition.

Example 4

The same procedure was performed as Example 1, except that 10 g of polyoxyethylene tristyryl ether phosphate (manufactured by Rodia Corporation, commercial name: Soprophor FLK) was used in place of 100 g of sodium alkylsulfate/EO 2 mol and that 159 g of aqueous gum arabic solution of 12.6% by weight was used in place of 249 g of aqueous gum arabic solution of 8% by weight, to afford a present composition.

Example 5

The same procedure was performed as Example 4, except that 10 g of polyoxyethylene aliphatic alcohol (manufactured by Clariant Company, commercial name: Genapol C100) was used in place of polyoxyethylene tristyryl ether phosphate, to afford a present composition.

Example 6

The same procedure was performed as Example 4, except that 10 g of aliphatic alcohol ethersulfate sodium salt (manufactured by Clariant Company, commercial name: Genapol LRO paste) was used in place of polyoxyethylene tristyryl ether phosphate, to afford a present composition.

Example 7

The same procedure was performed as Example 4, except that 10 g of silicone type surfactant (manufactured by Nihon Unicar, commercial name: Silwet 560) was used in place of polyoxyethylene tristyryl ether phosphate, to afford a present composition.

Example 8

The same procedure was performed as Example 4, except that 6 g of tristyryl phenyl sulfate (manufactured by Rodia Corporation, commercial name: Soprophor TSS) was used in place of 10 g of polyoxyethylene tristyryl ether phosphate and that 163 g of aqueous gum arabic solution of 12.3% by weight was used in place of 159 g of aqueous gum arabic solution of 12.6% by weight, to afford a present composition.

Example 9

The same procedure was performed as Example 4, except that tristyryl phenyl type surfactant/EO 20 mol (manufactured by Clariant Company, commercial name: Emulsogen 3474) was used in place of polyoxyethylene tristyryl ether phosphate, to afford a present composition.

Example 10

The same procedure was performed as Example 4, except that 3 g of phosphate ester type surfactant/EO.PO.EO block polymer (manufactured by Clariant Company, commercial name: Dispergermittel 3618) was used in place of 10 g of polyoxyethylene tristyryl ether phosphate and that 166 g of aqueous gum arabic solution of 12% by weight was used in place of 159 g of aqueous gum arabic solution of 12.6% by weight, to afford a present composition.

Example 11

The same procedure was performed as Example 10, except that 3 g of alcohol PO.EO block polymer (manufactured by Clariant Company, commercial name: Emulsogen 3510) was used in place of 3 g of phosphate ester type surfactant/EO.PO.EO block polymer, to afford a present composition.

Example 12

In 150 g of aromatic hydrocarbon (manufactured by ExxonMobil Chemical, commercial name: Solvesso 200), 34.2 g of flumicrolac-pentyl and 1.2 g of isocyanate (manufactured by Sumitomo Bayer Urethane Company, commercial name: Sumidur N-3200) were dissolved to afford a homogeneous solution, which was added to 189.6 g of aqueous gum arabic solution of 6% by weight containing 3.2 g of ethylene glycol and stirred at 6000 rpm by T. K. Autohomomixer at room temperature for 10 minutes to afford droplets, and then stirred gently at 60° C. for 20 hours. Then, addition of 125 g of water gave capsule suspension formulation containing 6.8% by weight of flumicrolac-pentyl. One hundred grams (100 g) of the obtained capsule suspension formulation were added to 900 g of Aerosil dispersion, which was obtained by stirring 32 g of fatty alcohol ethersulfate sodium salt (manufactured by Clariant Company, commercial name: Genapol LRO paste), 32 g of polyoxyethylene fatty alcohol (manufactured by Clariant Company, commercial name: Genapol C100), 16 g of methoxypropanol, 20 g of Aerosil COK-84 (mixture of anhydrous silica and alumina sol), 774.2 g of aqueous solution of glyphosate isopropylammonium salt (purity 62%) and 25.8 g of water, and stirred at 5000 rpm by T. K. Autohomomixer at room temperature for 10 minutes to afford a present composition.

Example 13

The same procedure was performed as Example 12, except that 72 g of silicone type surfactant (manufactured by Nihon Unicar, commercial name: Silwet 806) was used in place of 32 g of fatty alcohol ethersulfate sodium salt, 32 g of polyoxyethylene fatty alcohol and 16 g of methoxypropanol, and that 33.8 g of water was used in place of 25.8 g for preparing the dispersion, to afford a present composition.

Example 14

An aqueous gum arabic solution is prepared by dissolving 20 g of gum arabic (manufactured by San-eiyakuhin, commercial name: Arabiccol SS) in 237.9 g of water. To the gum arabic solution, 5 g of sodium alkylsulfate/EO 2 mol (manufactured by Rodia Corporation, commercial name: Rodapex N70K), 30 g of aliphatic alcohol polyglycol ether (manufactured by Clariant Company, commercial name: Emulsogen M), 30 g of aromatic hydrocarbon (manufactured by ExxonMobil Chemical Corporation, commercial name: Solvesso 200), 0.5 g of Antifoam CE (manufactured by Dow Corning Corporation), 50 g of polyethylene glycol, 774.2 g of aqueous glyphosate isopropylammonium salt solution (purity 62%), 20 g of silica/aluminum oxide mixture (manufactured by Degussa Huls, commercial name: Aerosil COK-84) and 2.4 g of flumioxazin are added and pulverized the mixture by dynomill to afford a present composition.

Example 15

The same procedure is performed as Example 15, except that methyl oleate is used in place of the aromatic hydrocarbon (manufactured by ExxonMobil Chemical, commercial name: Solvesso 200), to afford a present composition.

Example 16

In 80 g of benzyl acetate, 2.4 g of flumioxazin is dissolved to afford a homogeneous solution. The solution is emulsified and dispersed in a mixture of 207.9 g of aqueous gum arabic solution of 9.6% by weight, 5 g of sodium alkylsulfate/EO 2 mol (manufactured by Rodia Corporation, commercial name: Rodapex N70K), 30 g of aliphatic alcohol polyglycol ether (manufactured by Clariant Company, commercial name: Emulsogen M), 50 g of polyethylene glycol, 0.5 g of Antifoam CE (manufactured by Dow Corning Corporation) and 774.2 g of aqueous glyphosate isopropylammonium salt solution (purity 62%) by stirring at room temperature for 10 minutes at 5000 rpm using T. K. Autohomomixer. Under stirring by T. K. Autohomomixer (room temperature, 5000 rpm), 20 g of silica/aluminum oxide mixture (manufactured by Degussa Huls, commercial name: Aerosil COK-84) is added to the dispersion, and continued to stir at room temperature for 10 minutes (5000 rpm), to afford a present composition.

Example 17

The same procedure is performed as Example 14, except that flumiclorac-pentyl is used in place of flumioxazin, to afford a present composition.

Example 18

The same procedure is performed as Example 14, except that carfentrazone-ethyl is used in place of flumioxazin, to afford a present composition.

Example 19

The same procedure is performed as Example 14, except that sulfentrazone is used in place of flumioxazine, to afford a present composition.

Example 20

The same procedure is performed as Example 14, except that fluthiaset-methyl is used in place of flumioxazin, to afford a present composition.

Example 21

The same procedure is performed as Example 14, except that pyraflufen-ethyl is used in place of flumioxazin, to afford a present composition.

Example 22

The same procedure is performed as Example 14, except that cinidon-ethyl is used in place of flumioxazin, to afford a present composition.

Example 23

The same procedure is performed as Example 14, except that azafenidin is used in place of flumioxazin, to afford a present composition.

Example 24

The same procedure is performed as Example 14, except that lactofen is used in place of flumioxazin, to afford a present composition.

Example 25

The same procedure is performed as Example 14, except that biphenox is used in place of flumioxazin, to afford a present composition.

Example 26

The same procedure is performed as Example 14, except that butafenacyl is used in place of flumioxazin, to afford a present composition.

Example 27

Four grams (4 g) of flumioxazin, 16 g of glyphosate isopropylammonium salt, 10 g of polyoxyethylene sorbitan monooleate (manufactured by Toho Chemical Company, commercial name: Solvon T-20), 10 g of carboxymethyl-cellulose and 660 g of water were mixed and pulverized to afford a slurry. To 70 g of the obtained slurry, 30 g of aromatic hydrocarbon (manufactured by ExxonMobil Chemical, commercial name: Solvesso 200) was added and mixed to afford a present composition.

Reference Example 1

The same procedure was performed as Example 12, except that 60 g of polyoxyethylene beef tallow alkylamine (manufactured by Witco Corporation, commercial name: Witcamine TAM-45) was used in place of 32 g of fatty alcohol ethersulfate sodium salt, 32 g of polyoxyethylene fatty alcohol and 16 g of methoxypropanol, and that 45.8 g of water was used in place of 25.8 g for preparing the dispersion, to afford a reference composition.

Test Example 1

Each of the formulations obtained by Examples 1–13 and Reference Example 1 was placed in a glass bottle and kept at 60° C. for 5 days. The content of flumiclorac-pentyl was compared with soon after preparation and degradation ratio was calculated. The results were given in Table 1.

TABLE 1

| | Degradation ratio (60° C., 5 days) |
|---|---|
| Example 1 | 2% |
| Example 2 | 1% |
| Example 3 | 0% |
| Example 4 | 3% |
| Example 5 | 0% |
| Example 6 | 1% |

TABLE 1-continued

| | Degradation ratio (60° C., 5 days) |
|---|---|
| Example 7 | 1% |
| Example 8 | 0% |
| Example 9 | 0% |
| Example 10 | 1% |
| Example 11 | 0% |
| Example 12 | 0% |
| Example 13 | 0% |
| Reference Example 1 | 70% |

Reference Example 2

The same procedure was performed as Example 1, except that water was used in place of aqueous gum arabic solution of 8% by weight, to afford a reference composition.

Reference Example 3

The same procedure was performed as Example 2, except that water was used in place of aqueous gum arabic solution of 8% by weight, to afford a reference composition.

Test Example 2

Each of the formulations obtained by Examples 1–13 and Reference Examples 2–3 was placed in a plastic bottle and observed the homogeneousness of the formulation by eye estimation. The results were given in Table 2.

TABLE 2

| | Homogeneousness (eye estimation) |
|---|---|
| Example 1 | homogeneous |
| Example 2 | homogeneous |
| Example 3 | homogeneous |
| Example 4 | homogeneous |
| Example 5 | homogeneous |
| Example 6 | homogeneous |
| Example 7 | homogeneous |
| Example 8 | homogeneous |
| Example 9 | homogeneous |
| Example 10 | homogeneous |
| Example 11 | homogeneous |
| Example 12 | homogeneous |
| Example 13 | homogeneous |
| Reference Example 2 | heterogeneous (separated) |
| Reference Example 3 | heterogeneous (separated) |

Reference Example 4

The same procedure is performed as Example 27, except that 30 g of water is used in place of 30 g of the aromatic hydrocarbon, to afford a reference composition.

Test Example 3

Plastic vats (17 cm×12 cm×7 cm) were filled with upland field soil, and the seeds of common ragweed (*Ambrosia artemisiifolia*) were sowed therein, followed by cultivation of the weed in a greenhouse for 28 days. Each of the formulations obtained in Example 27 and Reference Example 4 is diluted with a designated amount of water and uniformly sprayed over the foliage of the weed by means of a small sprayer. Thereafter, the weed was further growth in the greenhouse for 7 days and the herbicidal activity was examined. The results are given in Table 3.

In Table 3, the herbicidal activity is evaluated at 11 levels with indices of 0 to 10, wherein 0 means that there was no or little difference in the degree of growth between the treated weeds and the untreated weeds at the time of evaluation, and 10 means that the weeds died completely or their growth was completely inhabited.

TABLE 3

| Formulations | Dosage (g/hectare) | Herbicidal Activity |
| --- | --- | --- |
| Example 27 | 40 + 400 | 10 |
| Reference Example 4 | 40 + 400 | 1 |

The present invention provides a highly stable aqueous herbicidal composition in which degradation of the active ingredient is suppressed. Therefore, the use of the present composition gives a high efficacy of the active ingredients as shown in Test example 3.

What is claimed is:

1. An aqueous herbicidal composition which comprises
   (a) a water-soluble pesticidal ingredient,
   (b) a water-insoluble pesticidal ingredient,
   (c) at least one selected from nonionic surfactants and anionic surfactants,
   (d) an anionic water-soluble polymer of gum arabic,
   (e) a hydrophobic organic solvent and
   (f) water.

2. The aqueous herbicidal composition according to claim 1, which comprises
   (a) 15 to 80% by weight of water-soluble pesticidal ingredient,
   (b) 0.1 to 30% by weight of water-insoluble pesticidal ingredient,
   (c) 0.1 to 30% by weight of at least one selected from nonionic surfactants and anionic surfactants,
   (d) 0.1 to 20% by weight of anionic water-soluble polymer,
   (e) 0.1 to 50% by weight of hydrophobic organic solvent and
   (f) water.

3. The aqueous herbicidal composition according to claim 1 or 2, wherein the water-soluble pesticidal ingredient is a herbicidal active ingredient, and the water-insoluble pesticidal ingredient is a herbicidal active ingredient inhibiting protoporphyrinogenoxidase.

4. The aqueous herbicidal composition according to claim 1 or 2, wherein the water-soluble pesticidal ingredient is an agriculturally acceptable salt of glyphosate, glufosinate or bialafos, and the water-insoluble pesticidal ingredient is a herbicidal active ingredient inhibiting protoporphyrinogenoxidase.

5. The aqueous herbicidal composition according to claim 1 or 2, wherein the water-soluble pesticidal ingredient is an agriculturally acceptable salt of glyphosate, glufosinate or bialafos, and the water-insoluble pesticidal ingredient is flumiclorac-pentyl, flumioxazin, carfentrazone-ethyl, sulfentrazone, fluthiaset-methyl, pyraflufen-ethyl, cinidon-ethyl, azafenidin, lactofen, biphenox or butafenacyl.

* * * * *